US011400112B2

(12) United States Patent
Mathews et al.

(10) Patent No.: US 11,400,112 B2
(45) Date of Patent: Aug. 2, 2022

(54) COMBINATION THERAPY FOR TREATMENT OF LEUKEMIA (71) Applicant: St George's Hospital Medical School, London (GB)

(72) Inventors: Vikram Mathews, Vellore (IN); Sanjeev Krishna, London (GB); Yolanda Sydney Augustin, London (GB)

(73) Assignee: St George's Hospital Medical School, London (GB)

( * ) Notice: Subject to any disclaimer, the term of this patent is extended or adjusted under 35 U.S.C. 154(b) by 0 days.

(21) Appl. No.: 16/962,494

(22) PCT Filed: Jan. 17, 2019

(86) PCT No.: PCT/GB2019/050124
§ 371 (c)(1),
(2) Date: Jul. 15, 2020

(87) PCT Pub. No.: WO2019/141988
PCT Pub. Date: Jul. 25, 2019

(65) Prior Publication Data
US 2020/0345770 A1 Nov. 5, 2020

(30) Foreign Application Priority Data

Jan. 17, 2018 (GB) ..................... 1800736

(51) Int. Cl.
*A61K 33/36* (2006.01)
*A61P 35/02* (2006.01)
*A61K 31/357* (2006.01)
*A61K 33/26* (2006.01)
*A61K 47/22* (2006.01)

(52) U.S. Cl.
CPC ............ *A61K 33/36* (2013.01); *A61K 31/357* (2013.01); *A61K 33/26* (2013.01); *A61K 47/22* (2013.01); *A61P 35/02* (2018.01)

(58) Field of Classification Search
CPC ...... A61K 33/36; A61K 31/357; A61K 33/26; A61K 47/22; A61P 35/02
See application file for complete search history.

(56) References Cited

U.S. PATENT DOCUMENTS

| 6,720,011 | B1 | 4/2004 | Zhang | |
|---|---|---|---|---|
| 2004/0101573 | A1 | 5/2004 | Zhang | |
| 2013/0317095 | A1* | 11/2013 | Mi | ............... C07C 57/145 514/450 |
| 2015/0133462 | A1 | 5/2015 | Singh et al. | |
| 2016/0175331 | A1 | 6/2016 | Civin et al. | |
| 2016/0367674 | A1 | 12/2016 | Goldberg et al. | |
| 2017/0340733 | A1* | 11/2017 | Cao | ................ A61K 31/404 |

FOREIGN PATENT DOCUMENTS

| CN | 103202835 | 7/2013 |
|---|---|---|
| CN | 103202836 | 7/2013 |
| CN | 103202837 | 7/2013 |
| CN | 104739824 | 7/2015 |
| EP | 2926812 | 10/2015 |
| WO | WO 03103588 | 12/2003 |
| WO | 2014082569 | 6/2014 |

OTHER PUBLICATIONS

Alex et al., (2014) "Arsenic Trioxide Resistance: More to it than Mutations in PML-RARa," Blood 124(21) 1-5.
Au et al., (2013) "Feasibility of oral arsenic trioxide treatment for acute promyelocytic leukemia during hemodialysis," Ann Hematol 92: 417-418.
Budhraja et al., (2017) "Modulation of Navitoclax Sensitivity by Dihydroartemisinin-Mediated MCL-1 Repression in BCR-ABL + B-Lineage Acute Lymphoblastic Leukemia," Clinical Cancer Research 23,24, 7558-7568.
Chen et al., (2017) "Dihydroartemisinin Sensitizes Human Lung Adenocarcinoma A549 Cells to Arsenic Trioxide via Apoptosis," Biol Trace Res 179: 203-212.
Cicconi et al., (2016) "Current management of newly diagnosed acute promyelocytic leukemia," Annals of Oncology 27(8) 1474-1481.
Coombs et al., (2015) "Acute promyelocytic leukemia: where did we start, where are we now, and the future", Blood Cancer Journal 6: e304.
De Kouchkovsky et al. (2016) "Acute myeloid leukemia: a comprehensive review and 2016 update," Blood Cancer Journal 6: e441.
Efferth et al., (2004) "Enhancement of Cytotoxicity of Artemisinis Toward Cancer Cells by Ferrous Iron," Free Radical Biology & Medicine 37(7): 998-1009.
Efferth et al., (2017) "Cancer combination therapies with artemisinin-type drugs," 139: 56-70.
Fiorillo et al., (2016) "Bedaquiline, an FDA-approved antibiotic, inhibits mitochondrial function and potently blocks the proliferative expansion of stem-like cancer cells (CSCs)", Aging 1593-1606.
Gohil et al., (2010) "Discovery and therapeutic potential of drugs that shift energy metabolism from mitochondrial respiration to glycolysis", Nature Biotechnology, 28(3): 249-255.
Hanahan and Weinberg (2011) "Hallmarks of Cancer: The Next Generation," Cell 144(5) 646-674.
Kasznicki et al., (2014) "Metformin in cancer prevention and theraoy," Ann Transl Med. 2(6) 57 2-11.
Lai & Singh (1995) "Selective cancer cell cytotoxicity from exposure to dihydroartemisiinin and holotransferrin," Cancer Letters 91: 41-46.

(Continued)

*Primary Examiner* — Shirley V Gembeh
(74) *Attorney, Agent, or Firm* — Rudy J. Ng; Bozicevic, Field & Francis LLP (57) ABSTRACT The present invention relates to the treatment of leukemia, (e.g. acute myeloid leukemia, AML) using a triple combination of: arsenic trioxide; iron; and an artemisinin, such as artesunate.

19 Claims, 8 Drawing Sheets

(56) References Cited

OTHER PUBLICATIONS

Li et al., (2014) "Artesunate possesses anti-leukemia properties that can be enhanced by arsenic trioxide," Leukemia & Lymphoma; 55(6): 1366-1372.
Lu et al., (2014) "Systemic hemin therapy attenuates blood-brain barrier disruption after intracerebral hemorrhage," Neurobiology of Disease 70 245-251.
Manz et al., (2016) "Iron and cancer: recent insights," Annals of New York Academy of Sciences 1368(1): 149-161.
Singh et al., (2014) "A screening based approach to circumvent tumor microenvironment-driven intrinsic to BCR-ABL + inhibitors in Ph+ acute lymphoblastic leukemia," J. Biomol Screen 19(1): 158-167.
Wang et al., (2012) "Dihydroartemisinin induces autophagy and inhibits the growth of iron-loaded human myeloid leukemia K562 cells via ROS toxicity," FEBS Open Bio 2: 103-112.
Wang et al., (2017) "Mechanistic Investigation of the Specific Anticancer Property of Artemisinin and Its Combination with Aminolevulinic Acid for Enhanced Anticolorectal Cancer Activity," ACS Cent, Sci. 3(7) 743-750.
Warburg, (1956) "On the Origin of Cancer Cells," Science 123(3191) 309.
Zhang & Gerhard (2009) "Heme Mediates Cytotoxicity from Artemisinin and Serves as a General Anti-Proliferation Target," PloS One 4(10) e7472 1-10.
Zhang et al., (2015) "Systematic identification of arsenic-binding proteins reveals that hexokinase-2 is inhibited by arsenic," PNAS 112(49): 15084-15089.
Zhang et al., (2015) "Identification of Arsenic Direct-Binding Proteins in Acute Promyelocytic Leukaemia Cells," Int J Mol Sci 16(11): 26871-26879.
Zhao et al., (2018) "Arsenic Trioxide and Artemisinin Act Synergistically to Kill Tumor Cells In Vitro," Anti-Cancer Agents in Medicinal Chemistry 8:2178-2186.
Search Report issued by UK IPO on priority application (GB 1800736.9) drawn up on Aug. 23, 2018.
International Search Report from PCT application (PCT/GB2019/050124) dated Mar. 27, 2019.
Balasundaram et. al., (2021) "Combining arsenic trioxide and mitocans selectively disrupts cellular energetics in acute myeloid leukemia", American Society of Hematology Abstract #2245, 1 page.
Chinese Clinical Yearbook of Oncology, edited by Editorial Board, Peking Union Medical College Press, Sep. 30, 2016, p. 397 (translation also supplied).
Luxian and Hu (2012) Essay Collection of Professor Cao Luxian's Career in Medicine for 60 Years, Military Medical Science Press, p. 474 (translation also supplied).
Mei Quanxi (2008) Handbook of Pharmacology of Modern Chinese Medicine and Clinical Applications, China Press of Traditional Chinese Medicine, pp. 272-274, (translation also supplied).
Zhang and Gerhard (2008) "Heme activates artemisinin more efficiently than hemin, inorganic iron, or hemoglobin", Bioorg. Med. Chem, 16, 7853-7861.
Yu Peng, (2017) "The Anti-AML Effect and its Mechanism of Artemisinin Derivative SM1044", Shanghai Jiao Tong University Master's Degree Thesis, Wanfang Data Knowledge Service Platform 6 pages (English translation 8 pages).

\* cited by examiner

COMBINATION THERAPY FOR TREATMENT OF LEUKEMIA

FIELD OF THE INVENTION

The present invention relates to the treatment of leukemia (for example, acute myeloid leukemia, AML) using a triple combination of: (i) arsenic trioxide, (ii) iron; and (iii) an artemisinin, such as artesunate.

BACKGROUND TO THE INVENTION

Leukemia is a cancer of the white blood cells. Types of leukemia include acute myeloid leukemia (AML), acute lymphoblastic leukemia (ALL), chronic myeloid leukemia (CML), chronic lymphocytic leukemia (CLL) and hairy cell leukaemia. In 2015, leukemia was reported as being present in over two million people worldwide and responsible for over 350,000 deaths. It is the most common type of cancer in children, with three quarters of leukemia cases in children being of the ALL type. However, about 90% of all leukemias are diagnosed in adults, with AML and CLL being most common in adults.

The current backbone therapy for acute myeloid leukemia (AML), for example, is the combination of daunorubicin and cytosine arabinoside, which are myelosuppressive and have a significant bystander effect on normal cells.

Acute promyelocytic leukemia (AML-M3; APL) is a subtype of AML in which therapy has evolved into one where conventional myelosuppressive therapy is no longer required, at least in the non-high risk subset. Instead a combination therapy with all-trans retinoic acid (ATRA) and arsenic trioxide (ATO) is used, which together induce differentiation of the malignant cell population along with relatively specific apoptosis of the malignant cell population. As a result, conventional side effects of chemotherapy such as recurrent cytopenia, alopecia and mucositis are not seen. The current anticipated cure rates in APL with this non-myelosuppressive regimen exceeds 90% in most studies. Nonetheless, in some APL patients treatment is confounded by drug resistance, for example ATO resistance.

Furthermore, in contrast to APL, the majority of patients with AML, particularly in adults, are destined to have disease recurrence after treatment, and this remains the major cause of mortality. Additionally, a substantial proportion of elderly patients with AML and those with significant co-morbidities at diagnosis cannot receive the standard intensive chemotherapy regimens due to their associated toxicity.

A major focus of research and rationalisation of the relapse rate in leukemia has been, first, on acquired somatic genetic and epigenetic mutation that confer resistance within a sub-clone against chemotherapy and, second, on the presence of a leukemia-initiating compartment (also called a leukemia stem cell population) that is inherently resistant to chemotherapy and persists as minimal residual disease. However, it is increasingly recognized that there are additional biological processes that can contribute to the recurrence of leukemia after conventional chemotherapy. Recognizing and investigating these novel mechanisms of resistance could lead to recognition of novel therapeutic targets.

There is a pressing need to develop novel therapeutic strategies for treating leukemias (including AML), particularly which combine high efficacy with specificity for malignant cells with reduced off target side effects. It would also be desirable to develop therapeutic strategies that are suitable for treating forms of leukemia (e.g. AML) that are currently associated with high disease recurrence, which are suitable for treating ATO-resistant leukemias, and/or which are suitable for treating patients for whom conventional chemotherapy regimens are not viable.

SUMMARY OF THE INVENTION

It has now been found that a combination of: (i) arsenic trioxide, (ii) iron; and (iii) an artemisinin; can be used to treat leukemia. It has also been found that such a triple combination therapy may give rise to benefits (e.g. synergistic benefits) compared with the effects conferred by the respective compounds alone or in "double" combinations (i.e., a combination of any two of the above active agents). Still further, it has been found that such a triple combination has a clinically acceptable toxicity profile, which may contrast with combination therapies using similar active agents, such as delta-aminolevulinic acid as an agent for increasing intracellular iron concentrations.

The present invention thus provides:

[1] A pharmaceutical composition which comprises: (a) arsenic trioxide; (b) iron; and (c) an artemisinin (e.g. artesunate); for use in treating leukemia (e.g. AML).

[2] Arsenic trioxide for use in treating leukemia (e.g. AML) by co-administration with iron and an artemisinin (e.g. artesunate).

[3] Iron for use in treating leukemia (e.g. AML) by co-administration with arsenic trioxide and an artemisinin (e.g. artesunate).

[4] An artemisinin (e.g. artesunate) for use in treating leukemia (e.g. AML) by co-administration with arsenic trioxide and iron.

[5] A method of treating a patient suffering from leukemia (e.g. AML), which method comprises co-administering to said patient arsenic trioxide, iron and an artemisinin (e.g. artesunate).

[6] A product comprising (a) arsenic trioxide, (b) iron, and (c) an artemisinin (e.g. artesunate), as a combined preparation for simultaneous, concurrent, separate or sequential use in the treatment of a patient suffering from leukemia (e.g. AML).

[7] Use of arsenic trioxide in the manufacture of a medicament for the treatment of leukemia (e.g. AML) by co-administration with iron and an artemisinin (e.g. artesunate).

[8] Use of iron in the manufacture of a medicament for the treatment of leukemia (e.g. AML) by co-administration with arsenic trioxide and an artemisinin (e.g. artesunate).

[9] Use of an artemisinin (e.g. artesunate) in the manufacture of a medicament for the treatment of leukemia (e.g., AML) by co-administration with arsenic trioxide and iron.

[10] A pharmaceutical composition which comprises: (a) arsenic trioxide; (b) iron; and (c) an artemisinin (e.g. artesunate).

[11] A kit of parts which comprises: (a) arsenic trioxide; (b) iron; and (c) an artemisinin (e.g. artesunate); wherein said components (a), (b) and (c) are each formulated in a separate pharmaceutical composition or wherein any two of the components (a), (b) and (c) are formulated together in a first pharmaceutical composition and the remaining component is formulated in a second pharmaceutical composition.

Further aspects of the present invention are outlined in detail below.

BRIEF DESCRIPTION OF THE FIGURES

Y-axis corresponds to relative fluorescence intensity [RFU 590 nm/530 nm] and the bars along the x-axis are, from left to right, the results for the ATO-sensitive NB4 cell line, an ATO-resistant APL cell line generated from NB4 ("NB4-EVAsR1"), and the innately ATO-resistant UF1 cell line. The figure shows that the basal level of mitochondrial membrane potential of the ATO-resistant cell lines is significantly lower than for NB4 naïve cells (n=4).

DETAILED DESCRIPTION

Definitions

As used herein, and unless otherwise specified, the term "pharmaceutically acceptable salt(s)", includes, but is not limited to, salts of acidic or basic moieties of compounds described herein (including, but not limited to, artemisinin, artesunate, delta-aminolevulinic acid and iron). Basic moieties are capable of forming a wide variety of salts with various inorganic and organic acids. The acids that can be used to prepare pharmaceutically acceptable acid addition salts of such basic compounds are those that form non-toxic acid addition salts, e.g., salts containing pharmacologically acceptable anions. Suitable organic acids include, but are not limited to, maleic, fumaric, benzoic, ascorbic, succinic, acetic, formic, oxalic, propionic, tartaric, salicylic, citric, gluconic, lactic, mandelic, cinnamic, oleic, tannic, aspartic, stearic, palmitic, glycolic, glutamic, gluconic, glucaronic, saccharic, isonicotinic, methanesulfonic, ethanesulfonic, p-toluenesulfonic, benzenesulfonic acids, or pamoic (e.g., 1,1'-methylene-bis-(2-hydroxy-3-naphthoate)) acids. Suitable inorganic acids include, but are not limited to, hydrochloric, hydrobromic, hydroiodic, sulfuric, phosphoric, or nitric acids. Compounds that include an amine moiety can form pharmaceutically acceptable salts with various amino acids, in addition to the acids mentioned above. Chemical moieties that are acidic in nature are capable of forming base salts with various pharmacologically acceptable cations. Examples of such salts are alkali metal or alkaline earth metal salts and, particularly, calcium, magnesium, sodium, lithium, zinc, potassium, or iron salts.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, greater than about 98% by weight of one stereoisomer of the compound and less than about 2% by weight of the other stereoisomers of the compound or greater than about 99% by weight of one stereoisomer of the compound and less than about 1% by weight of the other stereoisomers of the compound.

As used herein and unless otherwise indicated, the term "stereomerically enriched" means a composition that comprises greater than about 55% by weight of one stereoisomer of a compound, greater than about 60% by weight of one stereoisomer of a compound, greater than about 70% by weight, or greater than about 80% by weight of one stereoisomer of a compound.

As used herein, and unless otherwise indicated, the term "enantiomerically pure" means a stereomerically pure composition of a compound having one chiral center. Similarly, the term "enantiomerically enriched" means a stereomerically enriched composition of a compound having one chiral center.

The Artemisinin

Artemisinin is a well known compound having the structure

Artemisinin and its derivatives (collectively referred to herein as "an artemisinin") have been widely used as medications in the treatment of malaria.

The active metabolite of artemisinin itself and artemisinins in general is dihydroarteminisin (DHA), which has the formula Non-limiting examples of artemisinins include artesunate, artemisinin, artemether, arteether, artelinic acid, artemotil, artemisone and dihydroarteminisin. Thus, in the present invention, the artemisinin can, for example, be a compound selected from the group consisting of artesunate, artemisinin, artemether, arteether, artelinic acid, artemotil, artemisone and dihydroarteminisin.

The chemical structure of artesunate is

Artesunate has a hemisuccinate group which confers substantial water-solubility and high oral bioavailability on the compound. In the present invention the artemisinin is preferably artesunate.

Previous studies have posited that artemisinins (including artesunate) may have anti-cancer properties. For example, pre-clinical studies of the antileukemic activity of artesunate are described in Leukemia Research, 59, 2017, 124-135.

Artemisinins such as artesunate can be conveniently administered by various means, including parenterally (e.g. intramuscular intravenously or intrarectally) and orally.

The artemisinin can be administered as such or in any physiologically acceptable physical form. For example, the artemisinin can be in the form of a physiologically acceptable salt or solvate. In this regard, it is emphasised that the term "an artemisinin" as used herein embraces a physiologically acceptable salt or solvate thereof (e.g. "artesunate" embraces any physiologically acceptable salt or solvate thereof). The preparation of physiologically acceptable physical forms, including salts and solvates, of known drugs is a matter of routine in the art and the present application is not a primer on such methods. One common formulation of artesunate is as its sodium salt (i.e. sodium artesunate).

The artemisinin can also be in any enantiomeric form, e.g. racemic, enantiomerically/stereoisomerically enriched and/or enantiomerically/stereoisomerically pure.

Arsenic Trioxide

Arsenic trioxide, $As_2O_3$, is a known chemotherapeutic agent. For example, it has been marketed as the drug Trisenox for the treatment of acute promyelocytic leukemia.

Arsenic trioxide can, for example, conveniently be provided as a concentrate for solution for infusion, e.g. for dilution and subsequent intravenous administration. In another embodiment, the arsenic trioxide may be formulated for oral administration (for example, as described in Au et al. Ann Hematol (2013) 92: 417).

Delta-Aminolevulinic Acid

Delta-aminolevulinic acid (also known as 5-aminolevulinic acid) has the chemical formula It has been marketed, in the form of the hydrochloride salt, as the drug Ameluz for the treatment of actinic keratosis of mild to moderate severity on the face and scalp and of field cancerization.

In humans, delta-aminolevulinic acid is a precursor to heme. Delta-aminolevulinic acid goes through a series of transformations in the cytosol and is finally converted to Protoporphyrin IX inside the mitochondria. This protoporphyrin molecule chelates with iron in presence of enzyme ferrochelatase to produce Heme. Administration of delta-aminolevulinic acid can thus be used to increase intracellular heme levels and to increase intracellular iron concentrations.

Delta-aminolevulinic acid can be administered as such or in any physiologically acceptable physical form. For example, delta-aminolevulinic acid can be in the form of a physiologically acceptable salt or solvate. In this regard, it is emphasised that the term "delta-aminolevulinic acid" as used herein embraces a physiologically acceptable salt or solvate thereof. The preparation of physiologically acceptable physical forms, including salts and solvates, of known drugs is a matter of routine in the art and the present application is not a primer on such methods. As noted above, one common formulation of delta-aminolevulinic acid as its hydrochloride salt.

One surprising aspect of the present invention is the finding that direct administration of iron (e.g., in the form of an iron complex such as hemin) may, in the context of a triple combination also comprising arsenic trioxide and an artemisinin for treatment of leukemia, be associated with improved outcome, such as lower bystander toxicity/side effects, than a corresponding triple combination in which delta-aminolevulinic acid is utilised in place of iron.

Iron

Iron has been used in medicine for hundreds of years, particularly for treatment of anaemia. It is on the WHO's List of Essential Medicines.

For the avoidance of doubt, when iron is used as an active agent in accordance with the present invention, it can be in any physical form provided that it is capable of increasing intracellular iron concentrations in the individual to whom it is to be administered. Thus, reference herein to "iron" are not to be construed as being limited to elemental iron metal. For example, non-limiting acceptable forms of the iron active agent include elemental iron and pharmaceutically acceptable iron salts and iron complexes. Thus, the "iron" active agent can be in the form of an iron rich compound, provided of course that the compound is capable of delivering iron to the subject after administration, e.g. provided that it can increase intracellular iron concentration after administration.

Iron (II) sulphate is one well known and commercially available form of iron for medical uses. Iron (II) fumarate is another commonly used and exemplary form of medical iron. Both represent exemplary forms of iron for use in accordance with the present invention.

Further exemplary forms of iron include heme iron polypeptide (HIP), ferrous glycine sulphate, ferric carboxymaltose, iron dextrans, iron sucrose and iron isomaltoside.

In a preferred aspect of the present invention, the iron is in the form of an iron complex. Such a complex may, for instance, be an iron (II) complex or an iron (III) complex. A preferred class of iron complex is an iron porphyrin complex, e.g. an iron (III) porphyrin complex. A preferred class of porphyrin is a protoporphyrin IX or a derivative thereof. For instance, an iron complex (e.g. an iron (III) complex) of protoporphyrin IX is one preferred type of iron for use in the present invention. Hemin and hematin are exemplary such species, as are compounds in which the complexing anion (Cl$^-$ in hemin; OH$^-$ in hematin) is replaced by another pharmaceutically acceptable anion. In one currently preferred embodiment of the present invention, the iron active agent comprises hemin. Such iron complexes have surprisingly been found to be associated with low bystander toxicity/more acceptable side effect profiles in the triple combination therapy embodied by the present invention.

When iron is to be administered in accordance with the present invention, it can be prepared in any suitable form and formulated for administration by any suitable means. Common means of administering iron include oral administration and parenteral administration.

Administration of iron directly increases intracellular iron levels.

Combination of Active Ingredients The present invention involves the use of a triple combination of arsenic trioxide, iron and an artemisinin. The arsenic trioxide, iron and the artemisinin are herein referred to as "active ingredients" or "active agents".

In one aspect, the present invention provides a pharmaceutical composition that comprises: (a) arsenic trioxide; (b) iron; and (c) an artemisinin; for use in treating leukemia. Pharmaceutical compositions according to the invention will typically further comprise one or more pharmaceutically acceptable excipients or carriers.

The present invention extends to situations where the active ingredients discussed above are co-administered. When the active ingredients are co-administered they can be present either in a single pharmaceutical composition or in separate pharmaceutical compositions, including in separate pharmaceutical compositions optimized for administration either by the same mode or a different mode. For example, the active ingredients may both be administered orally, either in a single pharmaceutical composition or, more preferably, in separate pharmaceutical compositions.

For the avoidance of doubt, in the product comprising (a) arsenic trioxide, (b) iron, and (c) an artemisinin, as a combined preparation for simultaneous, concurrent, separate or sequential use, the product may comprise any of:
(i) a single pharmaceutical composition that comprises all of (a), (b) and (c);
(ii) two (separate) pharmaceutical compositions, wherein any two of (a), (b) and (c) are formulated together in a first pharmaceutical composition and the remaining component is formulated in a second pharmaceutical composition; or
(iii) three (separate) pharmaceutical compositions, wherein (a) is formulated in a first pharmaceutical composition, (b) is formulated in a second pharmaceutical composition and (c) is formulated in a third pharmaceutical composition Co-administration of the active ingredients according to the present invention includes simultaneous, separate and sequential administration.

In general, pharmaceutical compositions used in the invention may be suitable for administration by any mode known in the art, e.g. oral, mucosal (e.g., nasal, sublingual, vaginal, buccal, or rectal), parenteral (e.g., subcutaneous, intravenous, bolus injection, intramuscular, or intra-arterial), topical (e.g., eye drops or other ophthalmic preparations), transdermal, or transcutaneous administration.

For oral administration, the pharmaceutical compositions of the present invention may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

For ophthalmic administration the pharmaceutical compositions of the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the pharmaceutical compositions of the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

For topical administration the pharmaceutical compositions of the present invention may take the form of any formulation normally used for topical administration, in particular solutions, lotions, emulsions of liquid consistency, emulsions of semi-liquid consistency, emulsions of semi-solid consistency, emulsions of solid consistency, creams, gels or ointments. The emulsions are obtained by dispersion of an oil phase in water (O/W) or a water phase in oil (W/O). For example, some pharmaceutical compositions for topical administration contain an oil phase. Such pharmaceutical compositions may, for example, be water-in-oil emulsions (i.e. emulsions wherein the water is the dispersed phase and the oil in the dispersion medium) or be substantially non-aqueous.

Compositions for topical use in accordance with the invention may also contain one or more emollients, emulsifiers, thickeners and/or preservatives. The emollients are typically long chain alcohols, such as cetyl alcohol, stearyl alcohol and cetearyl alcohol; hydrocarbons such as petrolatum and light mineral oil; or acetylated lanolin. The total amount of emollient in the formulation is preferably about 5% to about 30%, and more preferably about 5% to about 10% by weight based on the total weight of the formulation. The emulsifier is typically a nonionic surface active agent, e.g., polysorbate 60 (available from Sigma Aldrich), sorbitan monostearate, polyglyceryl-4 oleate, and polyoxyethylene (4)lauryl ether or trivalent cationic. Generally the total amount of emulsifier is preferably about 2% to about 14%, and more preferably about 2% to about 6% by weight based on the total weight of the formulation. Pharmaceutically acceptable thickeners, such as Veegum™ K (available from R.T. Vanderbilt Company, Inc.), and long chain alcohols (i.e. cetyl alcohol, stearyl alcohol or cetearyl alcohol) can be used. The total amount of thickener present is preferably about 3% to about 12% by weight based on the total weight of the formulation. Preservatives such as methylparaben, propylparaben and benzyl alcohol can be present in the formulation.

Optionally, an additional solubilizing agent such as benzyl alcohol, lactic acid, acetic acid, stearic acid or hydrochloric acid can be included in the formulation. If an additional solubilizing agent is used, the amount present is preferably about 1% to about 12% by weight based on the total weight of the cream.

Optionally, the formulation can contain a humectant such as glycerin and skin penetration enhancers such as butyl stearate.

It is known to those skilled in the art that a single ingredient can perform more than one function in a composition, i.e., cetyl alcohol can serve both as an emollient and as a thickener.

The pharmaceutical composition of the invention optionally comprises an oil phase. In this case, typically the amount of oil in the composition is at least 10 wt. %, preferably at least 30 wt. %, more preferably at least 50 wt. %, more preferably at least 80 wt. %, based on the total weight of the composition. As used herein an oil phase is typically a liquid or solid phase which is substantially immiscible with water. More typically, an oil phase as used herein has a solubility in water at 25° C. of less than or equal to 1 mg/L, preferably less than 0.1 mg/L.

The oil phase in an emulsion may be any oil phase normally used in emulsions for topical administration. Such oil phases include, for example, hydrocarbon bases such as such as hard paraffin, soft paraffin, ceresine and microcrystalline wax, absorption bases such as lanolin and beeswax, emulsifying bases such as emulsifying wax and cetrimide, and vegetable oils such as olive oil, coconut oil, sesame oil, almond oil and peanut oil. Other oil phases useful in accordance with the invention are mineral oil, liquid petroleum, sorbitan monostearate, polysorbate 60, cetyl esters wax, cetearyl alcohol, benzyl alcohol and 2 octyldodecanol.

Those skilled in the art will understand that by varying the ratio of water to oil in an emulsion, the result could be deemed a lotion, a cream, or an ointment, by order of increasing proportion of oil. An emulsion comprising similar proportions of oil phase and water phase is usually deemed a cream, whereas an ointment will generally contain a substantially higher proportion of oil phase compared to water phase, for example greater than 60 wt. % oil phase, preferably greater than 70 wt. % oil phase, more preferably greater than 80 wt. % oil phase, based on the total weight of the oil phase and the water phase. A lotion will generally contain a lower proportion of oil phase than a cream, for example under 25 wt. % oil phase, under 20 wt. % oil phase, under 15 wt. % oil phase, under 10 wt. % oil phase or under 5 wt. % oil phase, based on the total weight of the oil phase and the water phase.

Generally, a cream for use according to the invention comprises an oil phase and a water phase mixed together to form an emulsion. Preferably, the amount of water present in a cream of the invention is about 45% to about 85% by weight based on the total weight of the cream, more preferably about 45 wt. % to about 65 wt. %, even more preferably about 45 wt. % to about 55 wt. %.

Where the composition is an ointment a pharmaceutically acceptable ointment base will be used. Examples of ointment bases include hydrocarbon bases such as such as hard paraffin, soft paraffin, ceresine and microcrystalline wax, absorption bases such as lanolin and beeswax, water-soluble bases such as polyethylene glycols (e.g. polyethylene glycol 200, 300, 400, 3350, 4000 or 6000), propylene glycol and polypropylene glycols, emulsifying bases such as emulsifying wax and cetrimide, and vegetable oils such as olive oil, coconut oil, sesame oil, almond oil and peanut oil. Mixtures of ointment bases can of course be used. The amount of ointment base present in an ointment of the invention is preferably about 60% to about 95% by weight based on the total weight of ointment, more preferably about 70 wt. % to about 90 wt. %, still more preferably about 75 wt. % to about 85 wt. %.

The pharmaceutical composition for use in accordance with the present invention may also be a lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

Parenteral administration to patients can be by various routes including, but not limited to, subcutaneous, intravenous (including bolus injection), intramuscular, and intraarterial. Because their administration typically bypasses patients' natural defences against contaminants, pharmaceutical compositions for parenteral administration are preferably sterile or capable of being sterilized prior to administration to a patient. Examples of such pharmaceutical compositions include, but are not limited to, solutions ready for injection, dry products ready to be dissolved or suspended in a pharmaceutically acceptable vehicle for injection, suspensions ready for injection, and emulsions.

Some suitable vehicles that can be used to provide pharmaceutical compositions for parenteral administration include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Suitable dosages of the active ingredients may be determined by a skilled medical practitioner. Actual dosage levels of the active ingredients may be varied so as to obtain an amount of the active ingredient which is effective to achieve the desired therapeutic response for a particular patient, composition, and mode of administration, without being toxic to the patient. Thus, the dosage is typically an effective or therapeutically effective dosage.

The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Dosage regimens may be adjusted to provide the optimum desired response. For example, a single dose may be administered (e.g. a single dose daily), several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

In the compositions and products according to the invention, the active ingredients may each, for example, be present at a concentration of between 0.001 and 20% by weight, relative to the total weight of the composition or product, preferably between 0.01 and 10%, more preferably between 0.02 and 5% by weight, and more preferably still between 1 and 4% by weight. In a particular embodiment, each of the three active ingredients is present at a concentration of between 1 and 3% by weight.

In one currently preferred aspect, the artemisinin (e.g., the artesunate) is formulated for administration at 50 to 500 mg (more preferably 100 to 300 mg such as about 200 mg) daily (based on a body weight of approximately 70 kg; dosages can be adjusted proportionally by body weight). Preferably, the artemisinin (e.g., the artesunate) is formulated for oral or parenteral administration. Preferably the artemisinin (e.g., the artesunate) is administered for a period of 3 to 30 days, more preferably 10 to 20 days, such as about 14 days. This period may correspond to a cycle of treatment in an administration regime that comprises multiple such cycles of treatment (e.g. at least two, three, four, five, six, or more cycles, for example with such cycles continuing until the desired therapeutic results have been achieved). Each cycle of treatment may be separated by a break in artemisinin (e.g., the artesunate) administration; such a break may, for example, allow for bone marrow recovery. The break in administration may comprise not administering the artemisinin (e.g., the artesunate) for a period of 3 to 14 days, more preferably 5 to 10 days, such as about 7 days.

In one exemplary such aspect, the artemisinin (e.g., the artesunate) is administered at about 200 mg daily for a cycle of treatment of two weeks, with each cycle being followed by a one week break.

In a currently preferred aspect, the arsenic trioxide is formulated for administration at 1 to 30 mg (more preferably 5 to 20 mg such as about 10 mg) daily (based on a body weight of approximately 70 kg; dosages can be adjusted proportionally by body weight). Preferably, the arsenic trioxide is formulated for parenteral or oral administration, most preferably for parenteral administration, e.g. for intravenous infusion. Preferably the arsenic trioxide is administered for a period of 3 to 60 days, more preferably 20 to 40 days, such as about 30 days. This period may correspond to a cycle of treatment in an administration regime that comprises multiple such cycles of treatment (e.g. at least two, three, four, five, six, or more cycles, for example with such cycles continuing until the desired therapeutic results have been achieved). Each cycle of treatment may be separated by a break in arsenic trioxide administration; such a break may, for example, allow for bone marrow recovery. The break in administration may comprise not administering the arsenic trioxide for a period of 3 to 14 days, more preferably 5 to 10 days, such as about 7 days.

In one exemplary such aspect, the arsenic trioxide is administered at about 10 mg daily for a cycle of treatment of 30 days, with each cycle being followed by a one week break.

In a currently preferred aspect, the iron is formulated for administration at 50 to 500 mg (more preferably 100 to 250 mg such as about 150 mg) daily. Preferably, the iron is formulated for oral or parenteral administration. Preferably the iron is administered for a period of 3 to 30 days, more preferably 10 to 20 days, such as about 14 days. This period may correspond to a cycle of treatment in an administration regime that comprises multiple such cycles of treatment (e.g. at least two, three, four, five, six, or more cycles, for example with such cycles continuing until the desired therapeutic results have been achieved). Each cycle of treatment may be separated by a break in iron administration; such a break may, for example, allow for bone marrow recovery. The break in administration may comprise not administering the iron for a period of 3 to 14 days, more preferably 5 to 10 days, such as about 7 days. In one exemplary such aspect, the iron is administered at about 200 mg daily for a cycle of treatment of two weeks, with each cycle being followed by a one week break.

As discussed elsewhere herein, in one embodiment of the invention the iron is provided in the form of an iron rich complex such as hemin. In a currently preferred aspect, the hemin is formulated for administration at 1-4 mg/kg/day IV infused over 10-15 minutes for 3-14 days based on the schedule. Preferably hemin is administered for a period of 3 to 25 days, more preferably 10 to 20 days, such as about 14 days. This period may correspond to a cycle of treatment in an administration regime that comprises multiple such cycles of treatment (e.g. at least two, three, four, five, six, or more cycles, for example with such cycles continuing until the desired therapeutic results have been achieved). Each cycle of treatment may be separated by a break in hemin administration; such a break may, for example, allow for bone marrow recovery. The break in administration may comprise not administering hemin for a period of 3 to 14 days, more preferably 5 to 10 days, such as about 7 days.

Additional Active Agents

Optionally, one or more additional active ingredients can be administered in addition to the arsenic trioxide, iron and the artemisinin. Thus, one or more additional active agents can be present in the products, pharmaceutical compositions and kits of the present invention. Examples of such additional active agents include cytarabine (cytosine arabinoside, or ara-C), anthracycline drugs such as doxorubicin, daunorubicin, daunomycin, idarubicin and mitoxantrone, other chemotherapeutic drugs such as Hydroxyurea (Hydrea®), Decitabine (Dacogen®), Cladribine (Leustatin®, 2-CdA), Fludarabine (Fludara®), Topotecan, Etoposide (VP-16) and 6-thioguanine (6-TG), corticosteroid drugs, such as prednisone or dexamethasone (Decadron®), methotrexate (MTX), 6-mercaptopurine (6-MP) or Azacitidine (Vidaza®), and other drugs such as all-trans-retinoic acid (ATRA), tretinoin, or Vesanoid®.

For example, the pharmaceutical composition as defined herein may additionally comprise one or more additional active agents. Further, each of: (a) the arsenic trioxide for use in treating leukemia by co-administration; (b) iron for use in treating leukemia by co-administration; and (c) the artemisinin for use in treating leukemia by co-administration; may additionally comprise co-administration with one or more additional active agents. Further, the method of treating a patient suffering from leukemia may comprise co-administering to said patient one or more additional active agents. Further, the product comprising (a) arsenic trioxide, (b) iron, and (c) an artemisinin, as a combined preparation for simultaneous, concurrent, separate or sequential use in the treatment of a patient suffering from leukemia may further comprise one or more additional active agents. Still further, the uses of the invention may comprise manufacture of a medicament for the treatment of leukemia by co-administration with one or more additional active agents. Still further, the kit of parts may comprise one or more additional active agents.

Treatment of Leukemia

Typically the patient to be treated is a mammal. Preferably the patient is a human.

In general, there is no limitation on the form of type of leukemia that is susceptible to treatment in accordance with the present invention. For example, the leukemia may be acute myeloid leukemia (AML). The leukemia may be acute lymphoblastic leukemia (ALL). The leukemia may be chronic myeloid leukemia (CML). The leukemia may be chronic lymphocytic leukemia (CLL). The leukemia may be hairy cell leukaemia.

In one preferred embodiment the leukemia is selected from AML and ALL. In another preferred embodiment the leukemia is selected from AML and CML. Particularly preferably the leukemia is AML.

Treatment of Acute Myeloid Leukemia

The present invention extends to the treatment of all sub-types of AML. For example, the WHO classification of AML includes the following sub-types:

Acute myeloid leukemia with t(8;21)(q22;q22), (AML1/ETO)

Acute myeloid leukemia with abnormal bone marrow eosinophils and inv(16)(p13q22) or t(16;16)(p13;q22), (CBFβ/MYH11)

Acute promyelocytic leukemia with t(15;17)(q22;q12), (PML/RARα) and variants (i.e. APL)

Acute myeloid leukemia with 11q23 (MLL) abnormalities

Acute myeloid leukemia with multilineage dysplasia

Following MDS or MDS/MPD

Without antecedent MDS or MDS/MPD, but with dysplasia in at least 50% of cells in 2 or more myeloid lineages Acute myeloid leukemia and myelodysplastic syndromes, therapy related Alkylating agent/radiation-related type Topoisomerase II inhibitor-related type (some may be lymphoid)

Acute myeloid leukemia, not otherwise categorized

Acute myeloid leukemia, minimally differentiated

Acute myeloid leukemia without maturation

Acute myeloid leukemia with maturation

Acute myelomonocytic leukemia

Acute monoblastic/acute monocytic leukemia

Acute erythroid leukemia (erythroid/myeloid and pure erythroleukemia)

Acute megakaryoblastic leukemia

Acute basophilic leukemia

Acute panmyelosis with myelofibrosis

Myeloid sarcoma.

In one embodiment, the AML is a form of AML other than APL (AML-M3), i.e. the AML is not APL. In another embodiment, the AML is APL.

The AML may be refractory AML. For example, the refractory AML may comprise a failure to achieve a complete remission or complete remission with incomplete blood recovery after a previous therapy. The refractory AML may be APL that is refractory to ATO (also known herein as ATO-resistant APL), e.g. failure to achieve a complete remission or complete remission with incomplete blood recovery after a previous therapy with ATO. Such a previous therapy with ATO may involve, for example, (i) treatment with ATO as a single active agent, and/or (ii) ATO in double combination with ART, and/or (iii) ATO in any combination other than the triple combination of ART, ATO and iron. ATO-resistance may be innate or acquired (i.e. arising in consequence of earlier treatment with ATO). If the refractory AML is not APL then inherently it will be resistant to ATO.

The term "complete remission" may be morphologically leukemia free state (i.e. bone marrow with <5% blasts by morphologic criteria and no Auer rods, no evidence of extramedullary leukemia) and absolute neutrophil count 1,000/µL and platelets>100,000/µL. The term "complete remission with incomplete blood recovery" may be morphologically leukemia free state (i.e. bone marrow with <5% blasts by morphologic criteria and no Auer rods, no evidence of extramedullary leukemia) and neutrophil count<1,000/µL or platelets<100,000/µL in the blood.

The AML may be relapsed AML. Relapsed AML may be associated with reappearance of leukemic blasts in the blood or >5% blasts in the bone marrow after complete remission not attributable to any other cause.

The patient to be treated may be a patient for whom established AML therapies are not viable (e.g. myelosuppressive therapy using, e.g., daunorubicin and/or cytosine arabinoside). For example, in one embodiment the patient to be treated is a patient having an age of 65 or above, preferably 72 or above, such as 80 or above and most preferably 85 or above. Alternatively or additionally, the patient to be treated may suffer from a co-morbidity that precludes myelosuppressive therapy such as using daunorubicin and/or cytosine arabinoside. Such patients may additionally have refractory AML (e.g. chemotherapy resistant AML or ATO resistant AML) and/or relapsed AML.

The present invention is explained in more detail in the following by referring to the Examples, which are not to be construed as limitative.

EXAMPLES

Example 1 (Reference)

Introduction

Metabolic reprogramming of cancer cells is one of the hallmarks of cancer and there is increasing evidence to suggest that metabolic plasticity of the cancer cells drives drug resistance in solid tumours. The malignant cells have been reported to be relying on glycolysis for their cell survival and proliferation, which is a less energy producing pathway in comparison to mitochondrial respiration. This behaviour of cancer cells is known as the Warburg effect: aerobic glycolysis where the cancer cells undergo glycolysis even in the presence of an ample amount of oxygen.

Malignant cells that are resistant to the conventional agents may be utilizing the mitochondrial respiration for survival, and agents which disrupt the metabolic adaptation have been reported to overcome resistance when combined with conventional agents. For example, comprehensive proteomics and metabolic studies of malignant cells treated with arsenic trioxide (ATO) have revealed that glycolysis is one among the key pathways that is significantly targeted and it could be one of the mechanisms of action of the anti-cancer effects of ATO.

It has previously been reported (Alex et al., Blood 2014 124(21) 3605) that ATO resistant cells have distinct metabolic features. It has now been hypothesised that ATO resistant cell lines (including non-M3 AML cells) rely on mitochondrial respiration for their survival.

Described herein are experiments demonstrating that combining ATO with inhibitors of oxidative metabolism can overcome ATO resistance and that the combinations of the present invention are effective against non-APL AML cells as well. In particular, the following experiments involve evaluation of the efficacy of these therapeutic agent combinations on in-house generated ATO resistant APL cell lines and against AML, cell lines and primary AML cells.

Figure 1:
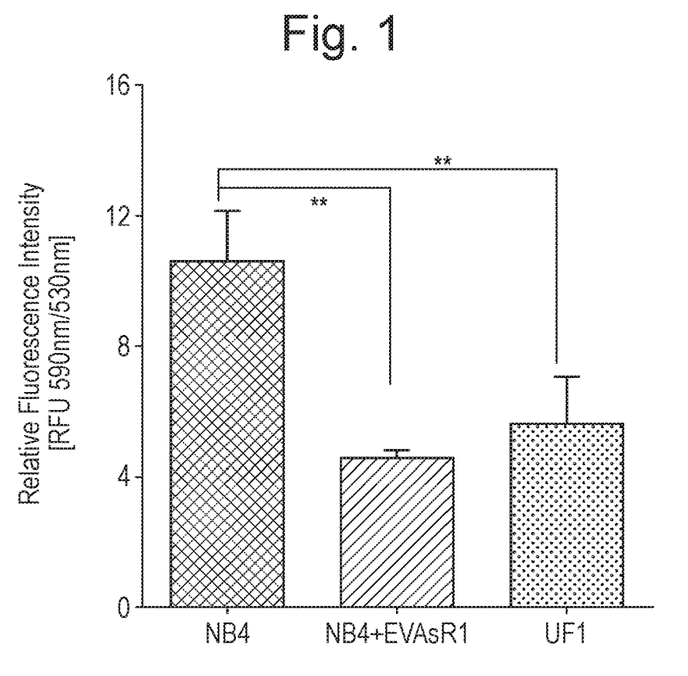
FIG. 1 shows basal levels of mitochondrial membrane potential of various cell lines, as described in Example 1.
Figure 2:
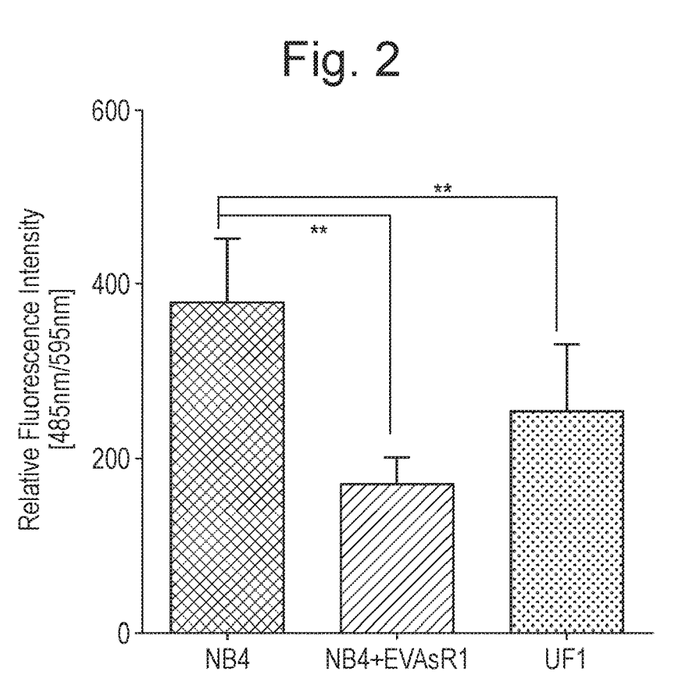
FIG. 2 shows basal amounts of glucose uptake for various cell lines, as described in Example 1. Y-axis corresponds to relative fluorescence intensity [RFU 485 nm/595 nm] and the bars along the x-axis are, from left to right, the results for the ATO-sensitive NB4 cell line, an ATO-resistant APL cell line generated from NB4 ("NB4-EVAsR1"), and the innately ATO-resistant UF1 cell line. The figure shows that the basal amount of glucose uptake of the ATO-resistant cell lines is significant lower than for NB4 naïve cells (n=4).
Figure 3:
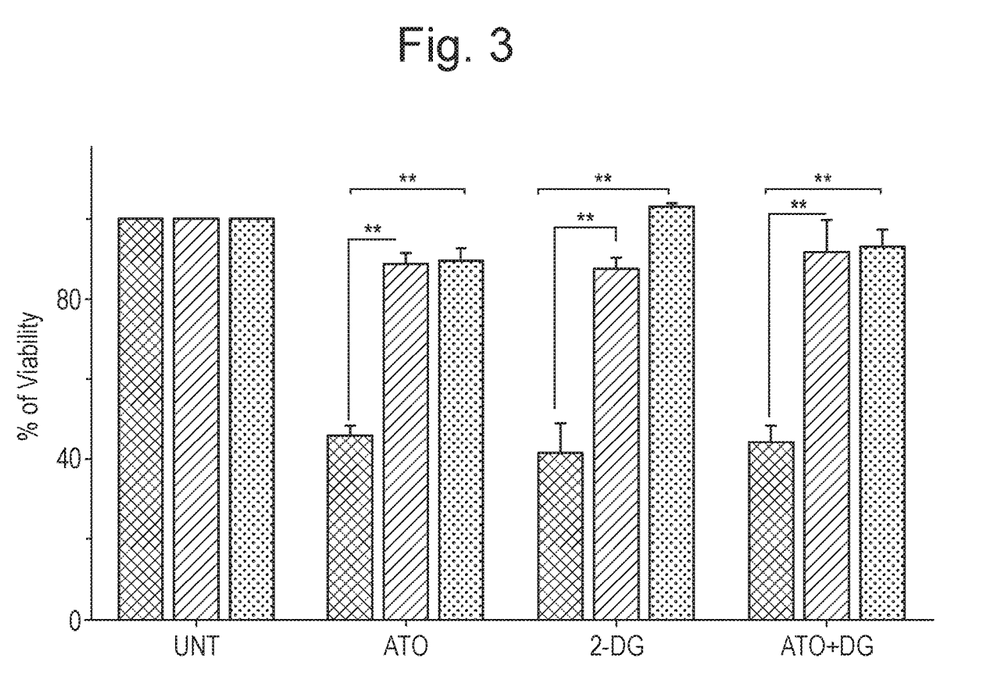
FIG. 3 shows the effect of the glycolytic inhibitor (i) 2-DG, (ii) ATO and (iii) the combination of 2-DG and ATO, on various cell lines, as described in Example 1 (n=4; time period=48 hours). Y-axis corresponds to % of viability. Four groups of three bars each are shown along the X-axis. For each group of three bars, the leftmost bar shows results for NB4 naïve cells, the central bar shows results for the ATO-resistant APL cell line generated from NB4 ("NB4-EVAsR1") and the rightmost bar shows results for the innately ATO-resistant UF1 cell line. From left to right, the groups correspond to: (i) untreated cells (i.e. control); (ii) treatment with ATO only; (iii) treatment with 2-DG only; and (iv) treatment with a combination of ATO and 2-DG; respectively.
Figure 4:
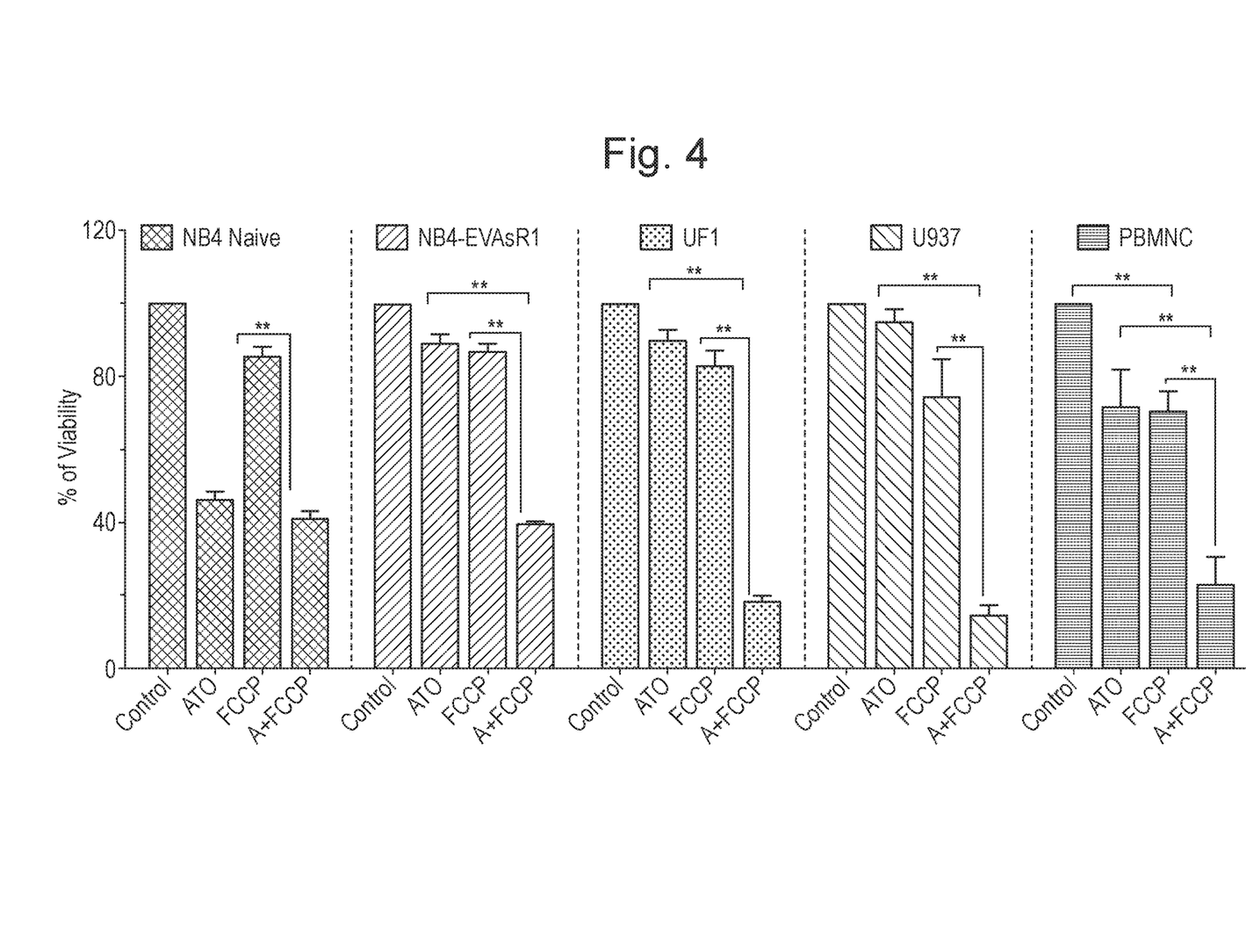
FIG. 4 shows the effect of (i) the OXPHOS uncoupler FCCP, (ii) ATO and (iii) the combination of FCCP and ATO, on various cell lines, as described in Example 1 (n=4; time period=48 hours). Y-axis corresponds to % of viability. Five groups of four bars each are shown along the X-axis. For each group of four bars, the individual bars correspond, from left to right, to: (i) untreated cells (control); (ii) treatment with ATO only; (iii) treatment with FCCP only; and (iv) treatment with a combination of ATO and FCCP; respectively. From left to right, the groups correspond to: (i) NB4 naïve cell line results; (ii) results for the ATO-resistant APL cell line generated from NB4 ("NB4-EVAsR1"); (iii) UF1 cell line results; (iv) U937 cell line results; and (v) effect on normal peripheral blood mononuclear cells (PBMNC); respectively.
Figure 5:
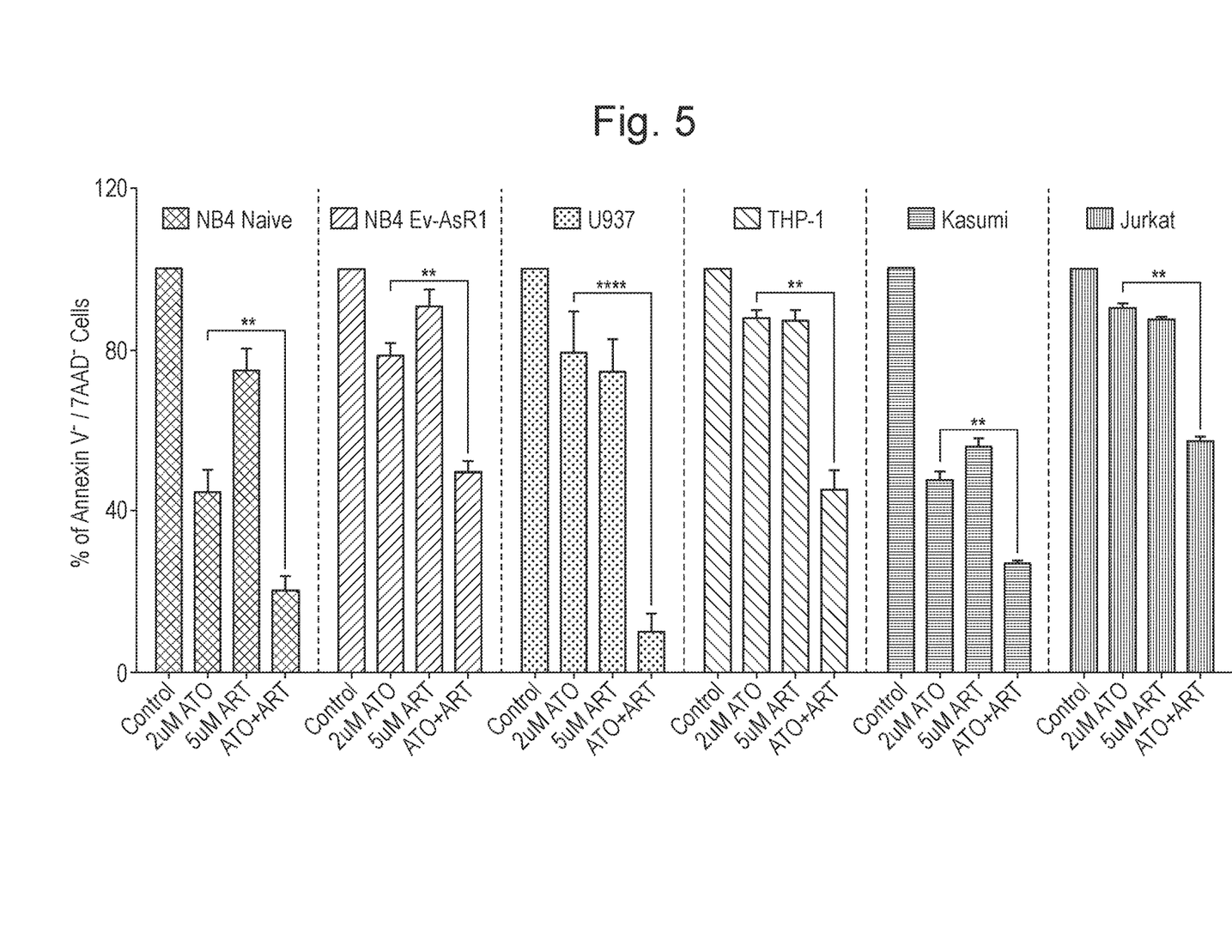
FIG. 5 shows the effect of (i) ATO, (ii) ART; and (iii) the combination of ATO and ART, on various cell lines, as described in Example 1 (n=8; time period=48 hours). Y-axis corresponds to % of Annexin $V^-$/7AAD$^-$ cells. Six groups of four bars each are shown along the X-axis. For each group of four bars, the individual bars correspond, from left to right, to: (i) untreated cells (control); (ii) treatment with 2 μM ATO only; (iii) treatment with 5 μM ART only; and (iv) treatment with a combination of ATO and ART; respectively. From left to right, the groups correspond to: (i) ATO-sensitive NB4 naïve cell line results; (ii) results for the ATO-resistant APL cell line generated from NB4 ("NB4-EVAsR1"); (iii) ATO-resistant U937 cell line results; (iv) ATO-resistant THP-1 cell line results; (v) ATO-sensitive Kasumi cell line results; and (vi) ATO-resistant Jurkat cell line results.
Figure 6:
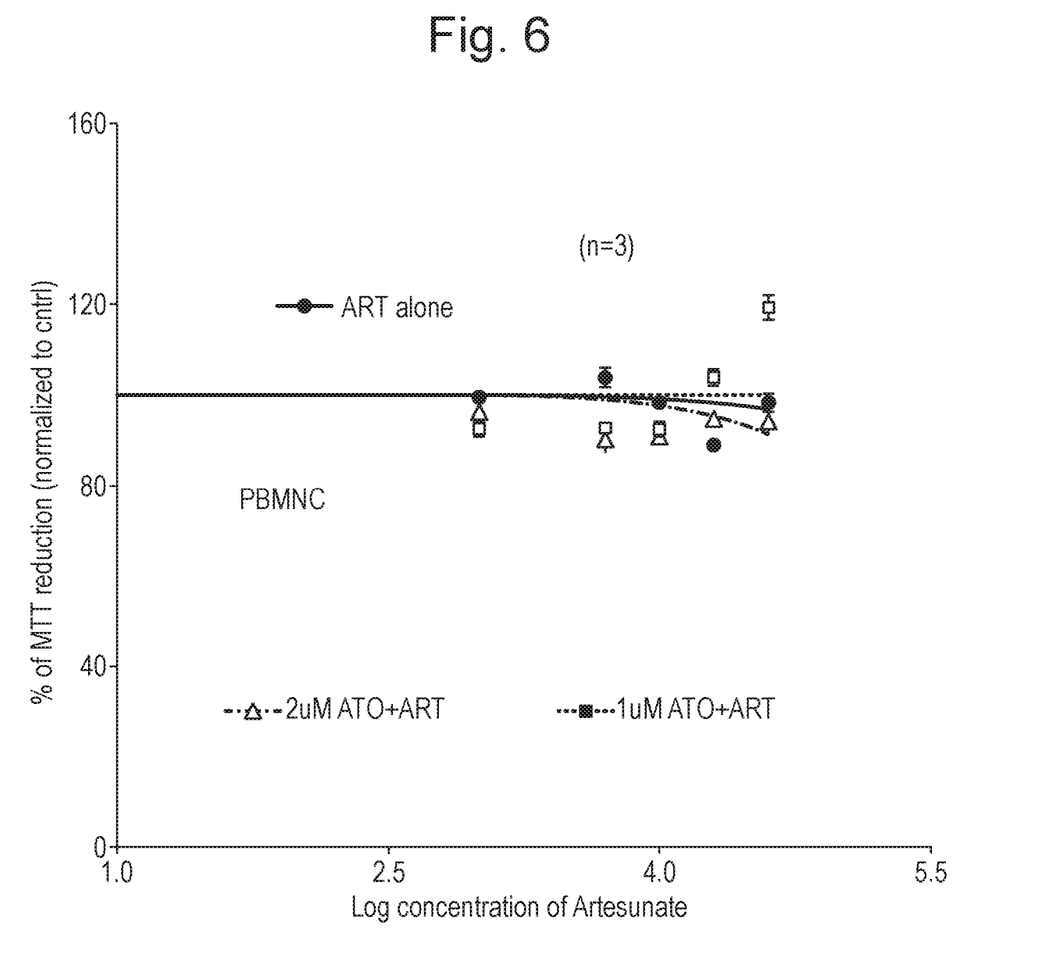
FIG. 6 shows the results of an in vitro cytotoxicity assay on normal PBMNCs where ATO was used at two different concentrations and ART in varying concentrations, as described in Example 1 (n=3; time period=48 hours). Y-axis corresponds to % of MTT reduction (normalised to control). X-axis corresponds to the log concentration of artesunate (μM). Results for ART alone are shown in circles with the line of best fit towards the right of the graph being in between the other two lines of best fit. Results for treatment with 1 μM ATO and ART are shown in squares with the line of best fit towards the right of the graph being the uppermost line. Results for treatment with 2 μM ATO and ART are shown in triangles with the line of best fit towards the right of the graph being the lowermost line.
Figure 7:
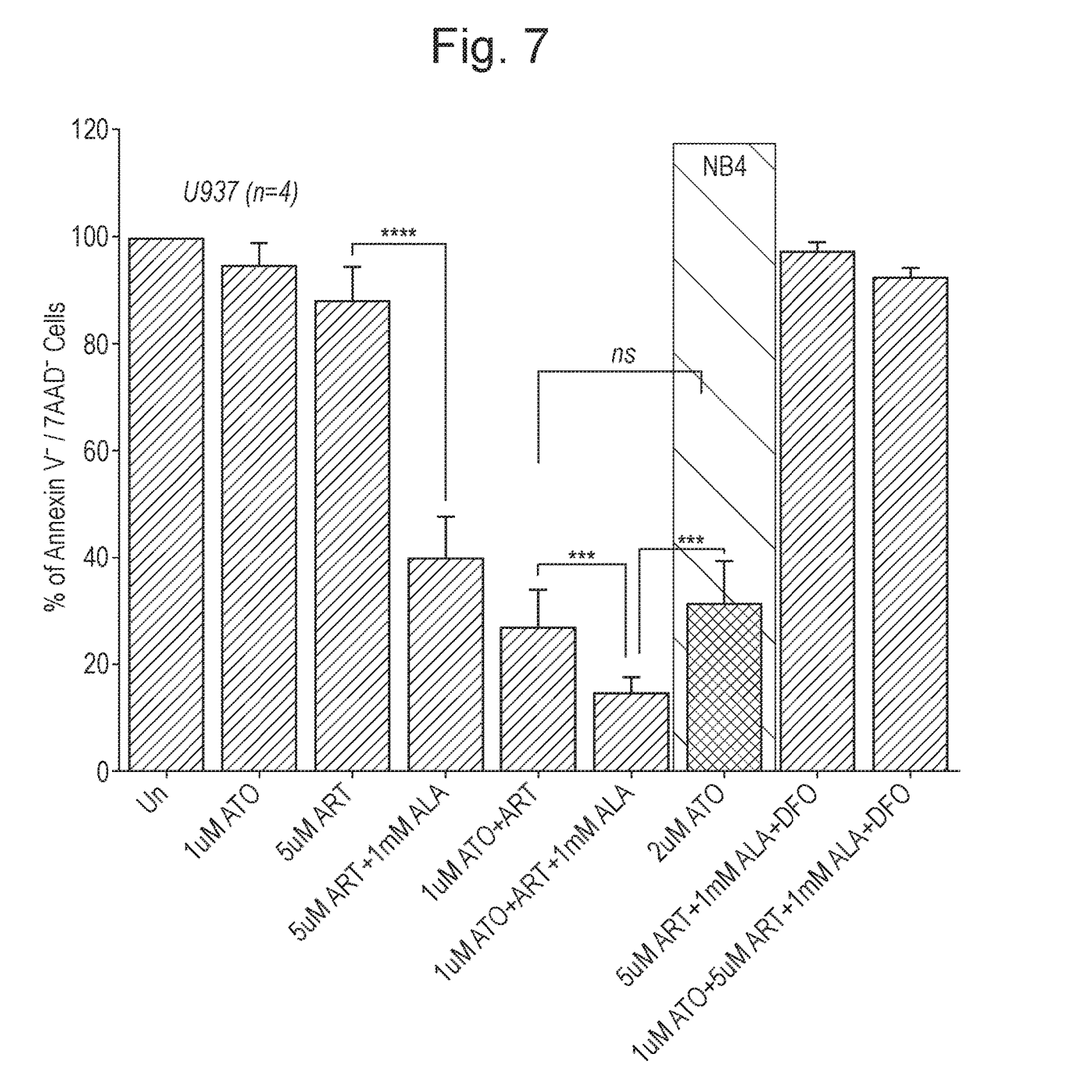
FIG. 7 shows the results, as described in Example 1 (n=4; time period=48 hours), of treatment of U937 cells with: (i) no treatment (control); (ii) ATO (1 μM); (iii) ART (5 μM); (iv) ART (5 μM) and ALA (1 mM); (v) ATO (1 μM) and ART (5 μM); (vi) ATO (1 μM) and ART (5 μM) and ALA (1 mM); (vii) ART (5 μM) and ALA (1 mM) and DFO (20 μM); and ATO (1 μM) and ART (5 μM) and ALA (1 mM) and DFO (20 μM). Also shown (third bar from the right) are the results of treatment NB4 naïve cells with ATO (2 μM). Y-axis corresponds to % of Annexin $V^-$/7AAD$^-$ cells.

Results i) It was observed that the resistant cell line, which was generated from the ATO sensitive promyelocytic cell line NB4, and a UF-1 cell line had significant distinguishing metabolic features compared with an NB4 naïve cell line such as decreased levels of reactive oxygen species (ROS), lower mitochondrial membrane potential (MMP) (FIG. 1), reduced glucose uptake (FIG. 2), decreased proliferation rates and increased glutathione levels.

ii) The sensitivity of these resistant cell lines was also measured to glycolytic inhibitor, given that the NB4 naïve cell lines are sensitive to the glycolytic inhibitor 2-Deoxy-D-glucose (2-DOG an analogue of glucose). It was observed (see FIG. 3) that, unlike the naïve NB4 cells, the ATO resistant cell lines were resistant to 2-DOG. The viability of the resistant cell lines was not significantly affected when the 2-DOG was combined with ATO. The data suggest that the ATO resistant cell lines are not relying on glycolysis for their proliferation and survival.

iii) The effect of mitochondrial oxidative phosphorylation (OXPHOS) inhibitor on these cell lines was then further evaluated. It was initially anticipated that the resistant cell lines viability would be significantly affected by FCCP (Carbonyl cyanide-4-(trifluoromethoxy)phenylhydrazone; an uncoupler of OXPHOS). However, it was observed that the viability of the resistant cell lines remained unaffected when FCCP was used as a single agent whereas a combination of FCCP and ATO significantly reduced the viability of resistant cell lines and there was no significant additive effect on naïve NB4 cells (FIG. 4). The combination not only reduced the survival of ATO resistant promyelocytic cells, but also innate ATO resistant myeloid and lymphoid leukemic cells such as U937 (FIG. 4), THP-1 and Jurkat E6.1 (data not shown). However, the effect of this combination on the malignant cells was not specific and it was also noted that there was a significant bystander effect on normal peripheral blood mononuclear cells (PBMNC; FIG. 4). These observations suggested that naïve ATO sensitive cells are dependent on glycolytic pathway for survival while ATO resistant cell lines have the ability to switch between the two energy producing pathways efficiently when one is inhibited. In summary these observations suggested that, in contrast to sensitive NB4 naïve cells, ATO resistant (acquired and innate) leukemic cells were more dependent on mitochondrial oxidative metabolism (reverse Warburg effect).

iv) As the combination had a significant bystander effect on the normal cells as compared to the malignant cells, screening was conducted for molecules reported to target/disrupt metabolic adaption with a wider therapeutic index. In particular, the effects of Metformin, Dichloroacetate (DCA) and Artesunate (ART) in combination with arsenic trioxide were evaluated. All these agents as a single agent did not have a significant effect on the malignant cells. However, the combination of arsenic trioxide with ART showed a significant effect on the malignant cells (FIG. 5) whereas with metformin no significant differences were observed. In comparison to DCA (data not shown), ART in combination with arsenic trioxide had a significantly more profound effect on the malignant cells.

v) It was also evaluated whether the combination of ATO and ART affects normal peripheral blood mono nuclear cells and it was observed that there is no significant bystander effect on these cells, unlike that which was observed with FCCP, a non-specific OXPHOS un-coupler (FIG. 6).

vi) In malaria, it has been reported that iron/heme plays an important role by enhancing the anti-parasitic activity of ART. An experiment was conducted in which the intracellular heme levels were increased by treating the cells with delta-aminolevulinic acid (ALA; a non-proteinogenic amino acid that is the first compound in the porphyrin synthesis pathway leading to heme) in combination with ART and lower concentration of ATO (1 uM). It was observed that ART in combination with ALA resulted in a significant reduction in the viability of AML cells, implying that intracellular heme levels play an important role in the activity of ART. The viability was even more significantly reduced in triple combination with ATO (FIG. 7). The apoptotic activity was found to be abrogated by an iron chelator (Deferoxamine; "DFO"). ALA and DFO as single active agents did not affect of the viability of this ATO-resistant cell line significantly (data not shown in FIG. 7).

Methods i) In vitro cytotoxicity assay: $10^5$ cells/well were seeded in a 96 well plate and treated with increasing concentration of artesunate and arsenic trioxide and incubated for 48 hours. At the end of 48 hrs MTT was added, followed by SDS to solubilize the formazan crystals formed by the viable cells. The absorbance was measured on an ELISA plate reader SpectraMaxM4 (Molecular Devices) at a test wavelength of 570 nm and a reference wavelength of 630 nm to measure the optical density. The colorimetric signal obtained should be proportional to the viable cell number. An IC-50 value was generated if significant cytotoxicity was detected. The half-maximal inhibitory concentration (IC-50) values were generated using Graph Pad Prism5 software (La Jolla, Calif., USA).

ii) Apoptosis Assay: Leukemic cell lines were added ($2 \times 10^5$ cells/well) in 24-well plates and treated with different drugs reported to disrupt the metabolic adaptation of the leukemia cells along with appropriate controls. After 48 h of incubation at 37° C. $CO_2$ incubator, the viability of the leukemic cells was measured using an Annexin V/7-aminoactinomycin D (7AAD) apoptosis assay kit (BD Pharmingen, San Diego, Calif., USA) as per the manufacturer's protocol. The flow cytometry data were analysed using Cell Quest pro software (BD Biosciences, San Jose, Calif., USA).

iii) Measurement of Glucose Uptake: $5 \times 10^5$ cells were stained with 2-NBDG (fluorescent analogue of 2-Deoxyglucose) for 10 minutes, washed and the fluorescence measured at 485 nm/595 nm using Spectramax M4. The intensity is of the dye was represented as relative fluorescence intensity.

iv) Mitochondrial membrane potential: The mitochondrial membrane potential ($\Delta \psi m$) of the cells treated with drugs was measured using JC-1 dye (Life Technologies, Carlsbad, Calif., USA). The fluorescence intensity was measured using Spectramax M4 (Molecular Devices, Sunnyvale, Calif., USA) (green channel: excitation: 485 nm; emission: 530 nm; cut off 515 nm; red channel: excitation: 485 nm; emission: 590 nm; cut off 570 nm). The ratio of red to green fluorescence (590/530) was calculated and the $\Delta \psi m$ of treated cells compared with the untreated cells.

Example 2 (Triple Combination of Artesunate, Arsenic Trioxide and Iron Complex (Hemin))

The experiments described in Example 1 were repeated, but using the iron complex hemin instead of delta-aminolevulinic acid.

Figure 8A:
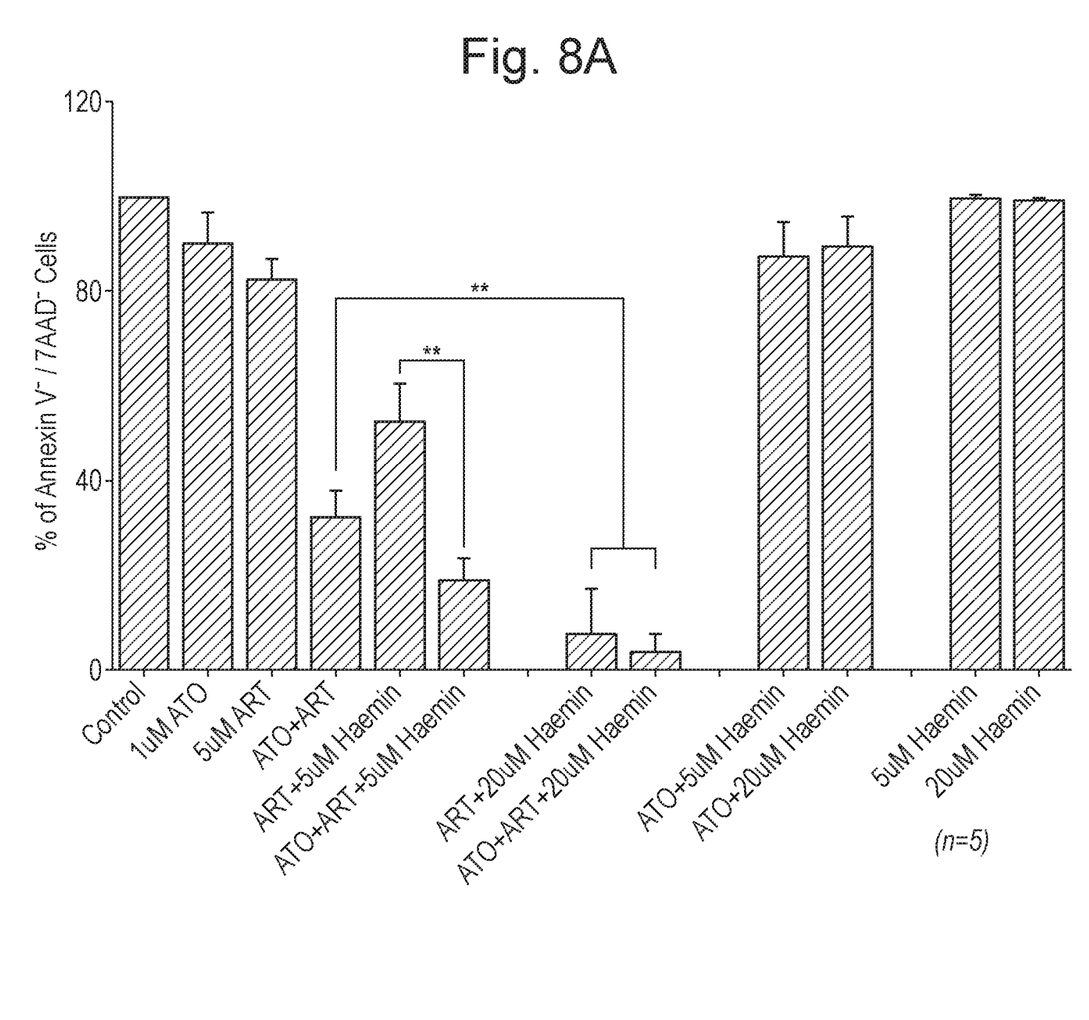
FIG. 8 shows the results, as described in Example 2 (n=5; time period=48 hours), of treatment of U937 cells. Panel A shows results of treatment with ATO, ART and/or hemin in various combinations and at various concentrations. Panel B shows the abrogation of potency by co-administration with DFO (for each pair of bars, the left-most bar shows results without DFO and the right-most bar shows results with DFO co-administration). The Y-axis in both panels corresponds to % of Annexin $V^-$/7AAD$^-$ cells.
Figure 8B:
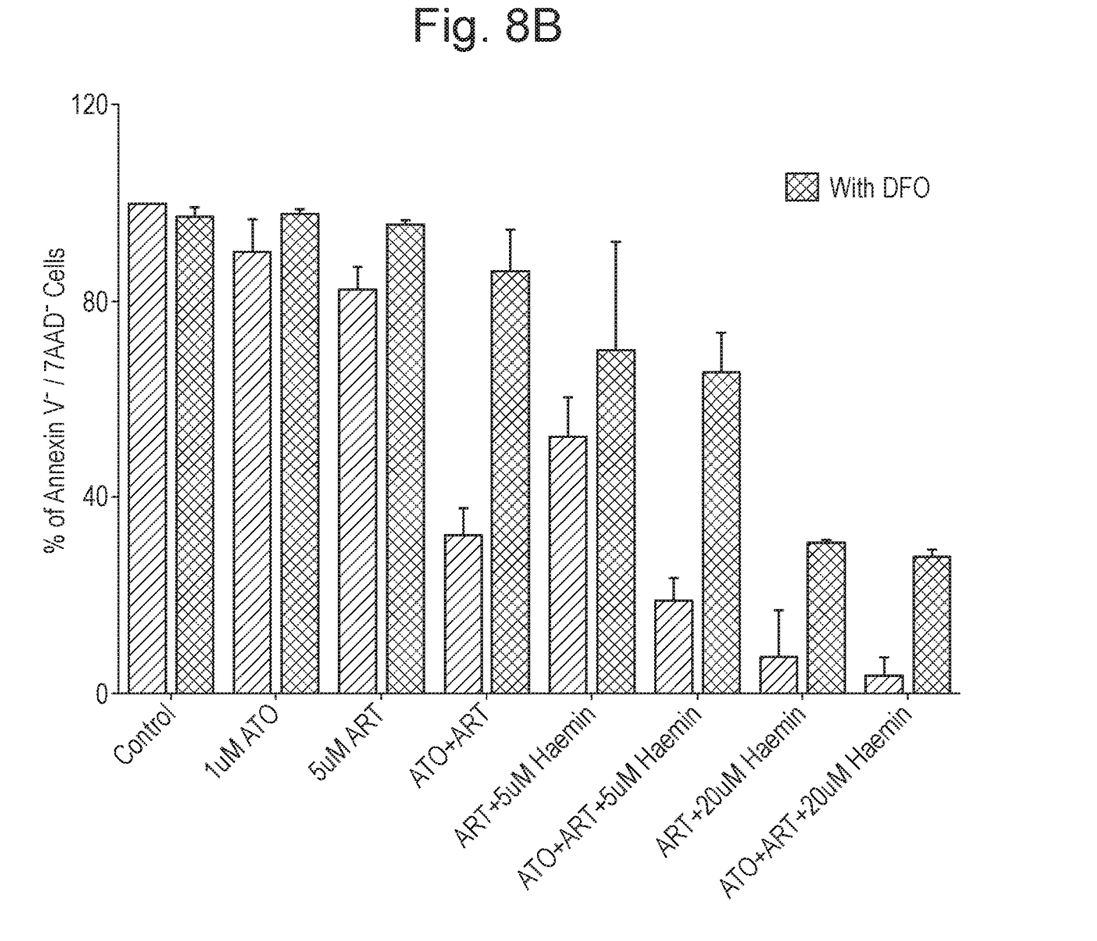

The results are shown in FIG. 8. It was observed that ART in combination with hemin resulted in a significant reduction in the viability of AML, cells. The viability was even more significantly reduced in triple combination with ATO. The apoptotic activity was found to be abrogated by an iron chelator (Deferoxamine; "DFO"). Hemin and DFO as single active agents did not affect of the viability of this ATO-resistant cell line significantly.

Example 3 (In Vivo Studies)

Summary

In vitro work suggested that there is a significant synergy between arsenic trioxide and artesunate. The effect of the combination was further enhanced by adding an iron enhancing agent such as alpha-aminolevulinic acid (ALA) or hemin. To further validate this in vitro observation, in vivo studies were performed on a mouse model of acute promyelocytic leukemia. The initial experiments with alpha aminolevulinic acid (ALA) demonstrated that there was significant toxicity related to the drug and its formulation in mice and hence it was opted to further evaluate this combination with hemin. In the absence of any existing literature on the use of hemin in the treatment of malignancy (cancers), the hemin dosage schedules from non-malignant studies (Lu, X., J. Chen-Roetling, and R. F. Regan, Systemic hemin therapy attenuates blood-brain barrier disruption after intracerebral hemorrhage. Neurobiology of disease, 2014. 70: p. 245-251) were adapted for these in vivo experiments.

Mouse Model and Drug Treatments

FVB/N mice were obtained from Jackson Laboratory (Bar Harbor, Me., USA). Mice at 6 to 8 weeks of age were used for experiments. The animal study design and euthanasia protocols were approved by the institutional animal ethics committee. Acute promyelocytic cells from the spleen of MRP8-PML-RAR transgenic mice (FVB/N) were harvested and cryopreserved for the leukemia development. APL cells ($5 \times 10^4$ cells/mouse) were injected intravenously via the tail vein into genetically compatible FVB/N recipients.

Drugs and Route of Administration

1. ATO was given intraperitoneally at the concentration of 5 mg/kg of mice starting on day 7 post injection of malignant cells and continued for 28 days.

2. Artesunate was given intraperitoneally at the concentration of 50 mg/kg of mice starting on day 7 post injection of malignant cells and continued for 28 days.

3. Hemin (PANHEMATIN) was given intraperitoneally 6 hours prior to ATO and Art treatment on Day 7 at a concentration of 26 mg/kg of mice.

After the injection period mouse were monitored for leukemia and survival.

It was observed that, even the hemin administration prior or post treatment of ATO and ART had a significant effect on the activity of the combination. Though there was no significant improvement in addition to the standard of care (ATO in the management of APL where the outcome is greater than 80%), but in comparison to the placebo there was a significant survival advantage in the combination of ATO+ART/ATO+ART+Hemin.

Results

The preliminary analysis suggests that there is significant benefit of this triple combination on leukemia regression and survival in mice.

The invention claimed is:

1. A method of treating a human patient suffering from leukemia, which method comprises co-administering to said patient arsenic trioxide at 0.014-0.429 mg/kg/day, iron at 0.714-7.143 mg/kg/day and an artemisinin at 0.714-7.143 mg/kg/day.

2. The method of claim 1, wherein said leukemia is acute myeloid leukemia (AML).

3. The method of claim 2, wherein said artemisinin is artesunate.

4. The method of claim 2, wherein said iron is an iron complex.

5. The method of claim 4, wherein said iron complex is a porphyrin complex.

6. The method of claim 5, wherein said porphyrin complex is hemin.

7. The method of claim 2, wherein said artemisinin is artesunate and said iron is hemin.

8. The method of claim 2, wherein said co-administering comprises simultaneously, separately or sequentially administering said arsenic trioxide, said iron and said artemisinin.

9. The method of claim 2, wherein said acute myeloid leukemia is arsenic trioxide resistant acute myeloid leukemia.

10. The method of claim 9, wherein said iron is hemin.

11. The method of claim 9, wherein said artemisinin is artesunate and said iron is hemin.

12. The method of claim 1, wherein said artemisinin is artesunate.

13. The method of claim 1, wherein said iron is an iron complex.

14. The method of claim 13, wherein said iron complex is a porphyrin complex.

15. The method of claim 14, wherein said porphyrin complex is hemin.

16. The method of claim 1, wherein said artemisinin is artesunate and said iron is hemin.

17. The method of claim 1, wherein said co-administering comprises simultaneously, separately or sequentially administering said arsenic trioxide, said iron and said artemisinin.

18. A pharmaceutical composition which comprises:
(a) arsenic trioxide formulated for administration at 0.014-0.429 mg/kg/day;
(b) iron formulated for administration at 0.714-7.143 mg/kg/day; and
(c) an artemisinin formulated for administration at 0.714-7.143 mg/kg/day.

19. A kit of parts which comprises:
(a) arsenic trioxide formulated for administration at 0.014-0.429 mg/kg/day;
(b) iron formulated for administration at 0.714-7.143 mg/kg/day; and
(c) an artemisinin formulated for administration at 0.714-7.143 mg/kg/day;
wherein said components (a), (b) and (c) are each formulated in a separate pharmaceutical composition or wherein any two of the components (a), (b) and (c) are formulated together in a first pharmaceutical composition and the remaining component is formulated in a second pharmaceutical composition.

* * * * *